(12) United States Patent
Yao et al.

(10) Patent No.: US 9,192,352 B2
(45) Date of Patent: Nov. 24, 2015

(54) ULTRASONIC DIAGNOSTIC APPARATUS, MEDICAL IMAGE DIAGNOSTIC APPARATUS, AND MEDICAL IMAGE PROCESSING METHOD

(71) Applicants: Cong Yao, Otawara (JP); Naohisa Kamiyama, Utsunomiya (JP); Kenji Hamada, Otawara (JP); Naoki Yoneyama, Otawara (JP)

(72) Inventors: Cong Yao, Otawara (JP); Naohisa Kamiyama, Utsunomiya (JP); Kenji Hamada, Otawara (JP); Naoki Yoneyama, Otawara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/726,864

(22) Filed: Dec. 26, 2012

(65) Prior Publication Data

US 2013/0165789 A1    Jun. 27, 2013

(30) Foreign Application Priority Data

Dec. 26, 2011 (JP) ................................ 2011-284385

(51) Int. Cl.
*A61B 8/08* (2006.01)
*A61B 8/06* (2006.01)
*A61B 5/0402* (2006.01)
*A61B 8/14* (2006.01)
*A61B 8/00* (2006.01)

(52) U.S. Cl.
CPC .............. *A61B 8/0891* (2013.01); *A61B 5/0402* (2013.01); *A61B 8/5223* (2013.01); *A61B 8/06* (2013.01); *A61B 8/14* (2013.01); *A61B 8/5207* (2013.01); *A61B 8/543* (2013.01)

(58) Field of Classification Search
CPC ...... A61B 5/0402; A61B 8/06; A61B 8/0891; A61B 8/14; A61B 8/5207; A61B 8/5223; A61B 8/543
USPC .................. 600/440, 441, 443, 447; 382/128
See application file for complete search history.

(56) References Cited

U.S. PATENT DOCUMENTS

| 2009/0076384 A1* | 3/2009 | Saad et al. .................... 600/437 |
| 2010/0063391 A1* | 3/2010 | Kanai et al. ................... 600/437 |
| 2010/0210946 A1* | 8/2010 | Harada et al. ................. 600/443 |
| 2012/0296214 A1* | 11/2012 | Urabe et al. .................. 600/444 |

FOREIGN PATENT DOCUMENTS

| CN | 1765330 A | 5/2006 |
| CN | 1921802 A | 2/2007 |
| CN | 101431942 A | 5/2009 |
| CN | 101505664 A | 8/2009 |
| CN | 102163326 A | 8/2011 |
| JP | 2009-160370 | 7/2009 |

OTHER PUBLICATIONS

Combined Office Action and Search Report issued May 28, 2014 in Chinese Patent Application No. 201210574742.6 (with English translation).

* cited by examiner

*Primary Examiner* — Michael Rozanski
(74) *Attorney, Agent, or Firm* — Oblon, McClelland, Maier & Neustadt, L.L.P.

(57) ABSTRACT

According to one embodiment, an ultrasonic diagnostic apparatus comprises a data acquisition unit, an image generation unit, a calculation unit, a determination unit and a measurement unit. The data acquisition unit acquires a plurality of ultrasonic data. The image generation unit generates a plurality of ultrasonic images by using the plurality of ultrasonic data. The calculation unit calculates a feature amount for determining a shift between the two-dimensional section and a central axis of a target blood vessel. The determination unit determines an optimal image from the plurality of ultrasonic images based on the feature amount. The measurement unit measures an intima-media thickness of the target blood vessel by using the optimal image.

20 Claims, 9 Drawing Sheets

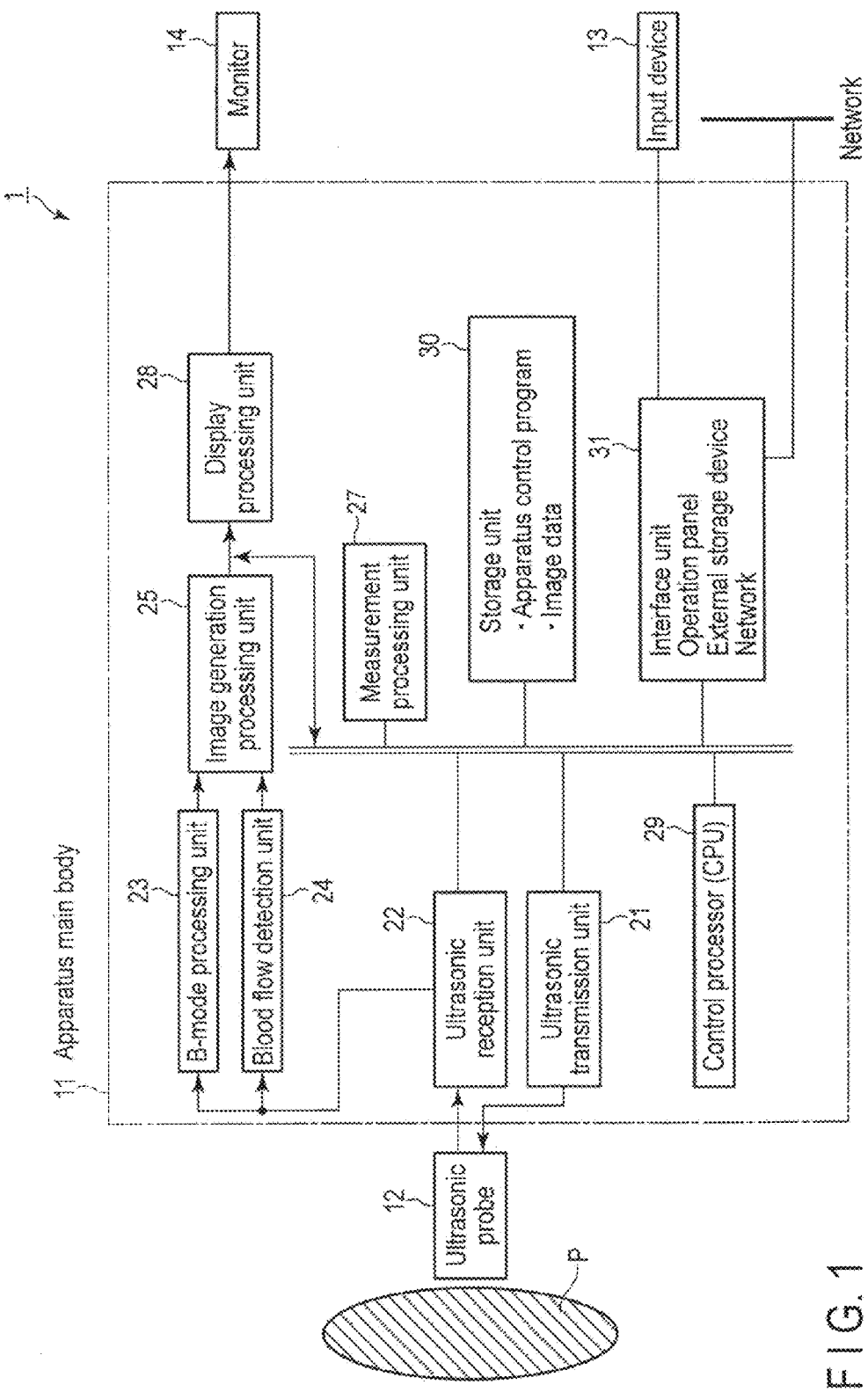
F I G. 1

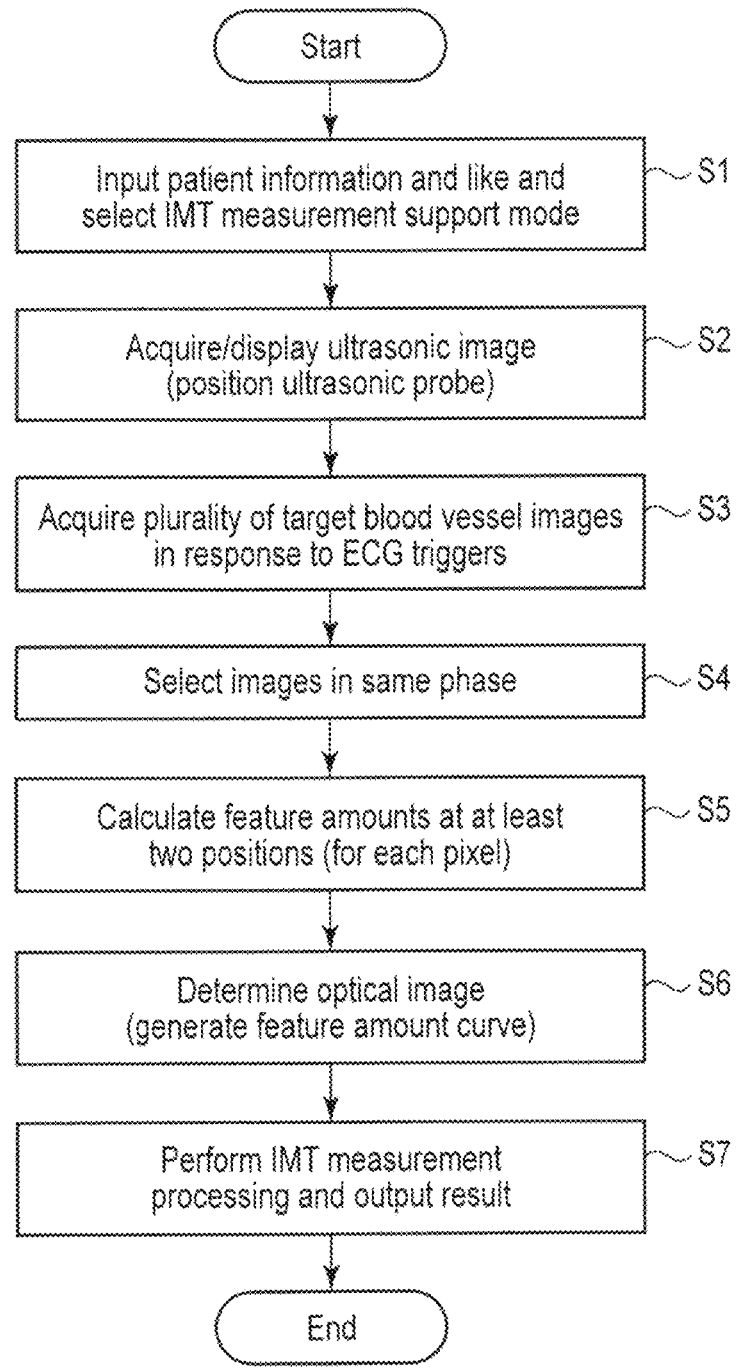
F I G. 2

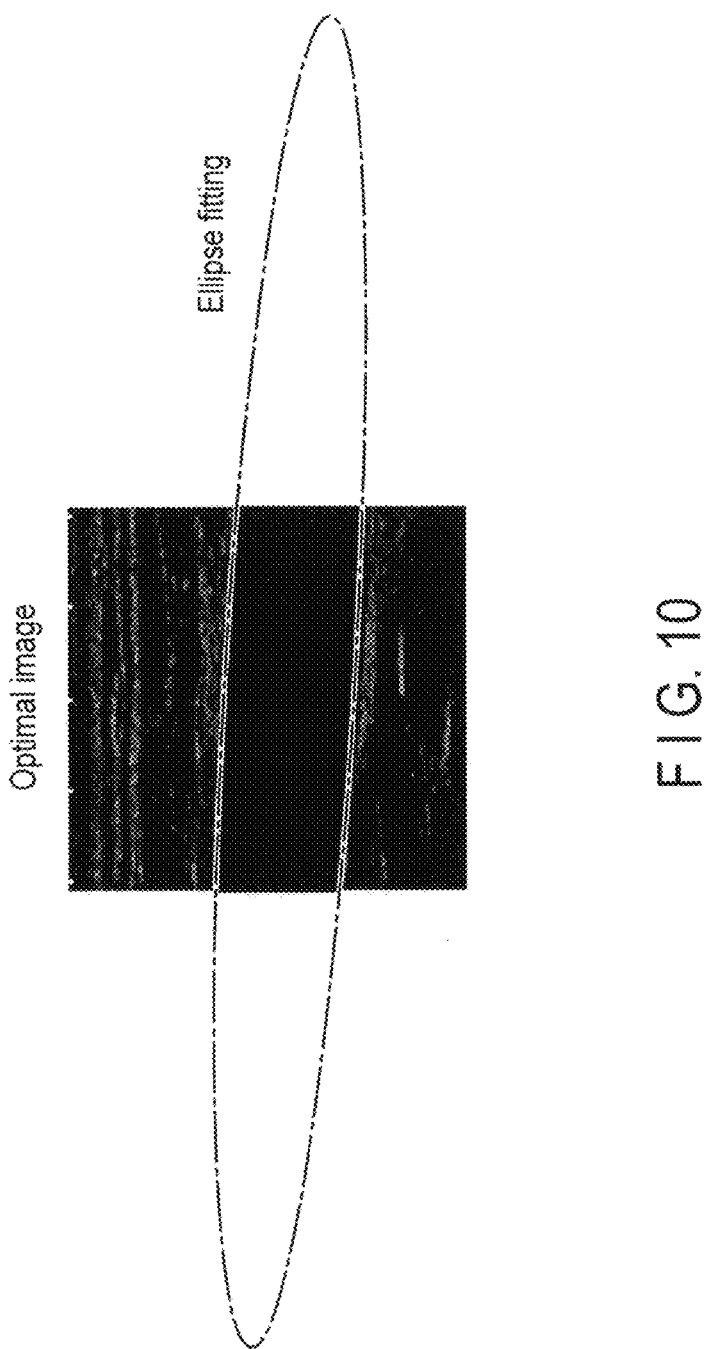
F I G. 10

ULTRASONIC DIAGNOSTIC APPARATUS, MEDICAL IMAGE DIAGNOSTIC APPARATUS, AND MEDICAL IMAGE PROCESSING METHOD

CROSS-REFERENCE TO RELATED APPLICATIONS

This application is based upon and claims the benefit of priority from Japanese Patent Application No. 2011-284385, filed Dec. 26, 2011, the entire contents of which are incorporated herein by reference.

FIELD

Embodiments described herein relate generally to an ultrasonic diagnostic apparatus, medical image diagnostic apparatus, and medical image processing method.

BACKGROUND

Consider, for example, an ultrasonic diagnostic apparatus or the like which is used to perform diagnosis or the like to evaluate the IMT (Intima-Media Thickness) of the blood vessel.

Medical image diagnosis is to visually perform diagnosis by observing the medical images acquired and displayed by a medical image diagnostic apparatus such as an ultrasonic diagnostic apparatus, X-ray computed tomography apparatus, magnetic resonance imaging apparatus, X-ray diagnostic apparatus, or nuclear medicine diagnostic apparatus. For example, ultrasonic image diagnosis is to visually diagnose a tumor or the like by observing the ultrasonic images acquired and displayed by an ultrasonic diagnostic apparatus. In this case, the ultrasonic diagnostic apparatus is designed to acquire biological information by transmitting the ultrasonic pulses generated from the transducers provided in an ultrasonic probe into the body of an object and receiving the reflected ultrasonic waves generated by acoustic impedance differences in the object tissue via the transducers. This apparatus can display image data in real time by the simple operation of bringing the ultrasonic probe into contact with the surface of the body, and hence is widely used for morphological diagnosis and functional diagnosis of various organs.

Recently, diagnosis to evaluate the IMT of the blood vessel has been performed by using, for example, an ultrasonic diagnostic apparatus. In general, this diagnosis is executed in the following manner. First of all, the operator finely adjusts the probe to make a two-dimensional section (ultrasonic scan plane) to be ultrasonically scanned pass over the central axis of a blood vessel to be diagnosed (target blood vessel) while observing the image obtained by ultrasonically scanning the two-dimensional section including the target blood vessel, and stores a plurality of images corresponding to a plurality of phases in a cine memory. The operator then selects an image optimal for IMT measurement from the stored images by visual check or the like, and sets a region of interest. This apparatus automatically or manually calculates an IMT based on the set region of interest. When considering the influence of the pulsation of the heart, the operator selects a plurality of images corresponding to the same phase by using ECG waveforms and the like, and then selects an image optimal for optimal IMT measurement.

BRIEF DESCRIPTION OF THE DRAWINGS

FIG. 1 is a block diagram of an ultrasonic diagnostic apparatus 1 according to an embodiment;

FIG. 2 is a flowchart showing a procedure for IMT measurement support processing;

FIG. 10 is a view for explaining ellipse fitting processing for a blood vessel section;

DETAILED DESCRIPTION

Figure 3:
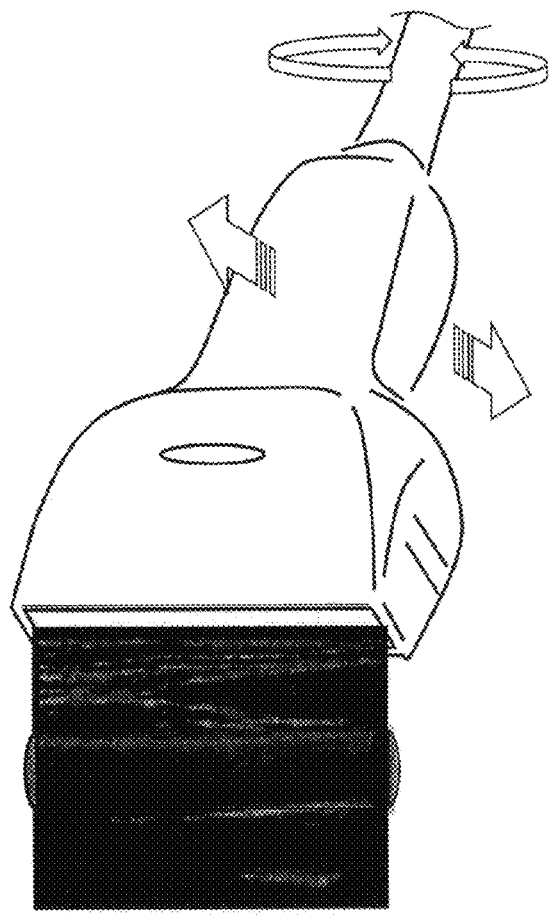
FIG. 3 is a view for explaining the adjustment of an ultrasonic scan plane by positioning of an ultrasonic probe.

In general, according to one embodiment, an ultrasonic diagnostic apparatus includes a data acquisition unit, image generation unit, determination unit, and measurement unit. The data acquisition unit acquires a plurality of ultrasonic data by repeatedly scanning a two-dimensional section including a target blood vessel with an ultrasonic wave. The image generation unit generates a plurality of ultrasonic images by using the plurality of ultrasonic data. The calculation unit calculates a feature amount for determining a shift between the two-dimensional section and a central axis of the target blood vessel in a running direction on each ultrasonic image. The determination unit determines an optimal image from the plurality of ultrasonic images based on the feature amount. The measurement unit measures an intima-media thickness of the target blood vessel by using the optimal image.

An embodiment will be described below with reference to the accompanying drawing. Note that the same reference numerals in the following description denote constituent elements having almost the same functions and arrangements, and a repetitive description will be made only when required.

FIG. 1 is a block diagram of an ultrasonic diagnostic apparatus 1 according to this embodiment. As shown in FIG. 1, the ultrasonic diagnostic apparatus 1 includes an ultrasonic probe 12, an input device 13, a monitor 14, an ultrasonic transmission unit 21, an ultrasonic reception unit 22, a B-mode processing unit 23, a blood flow detection unit 24, an image generation processing unit 25, a measurement processing unit 27, a display processing unit 28, a control processor (CPU)

29, a storage unit 30, and an interface unit 31. The function of each constituent element will be described below.

The ultrasonic probe 12 is a device (probe) which transmits ultrasonic waves to an object, and receives reflected waves from the object based on the transmitted ultrasonic waves. The ultrasonic probe 12 includes, on its distal end, an array of a plurality of piezoelectric transducers, a matching layer, a backing member, and the like. The piezoelectric transducers of the ultrasonic probe 12 transmit ultrasonic waves in a desired direction in a scan area based on driving signals from the ultrasonic transmission unit 21, and convert reflected waves from the object into electrical signals. The matching layer is an intermediate layer which is provided for the piezoelectric transducers to make ultrasonic energy efficiently propagate. The backing member prevents ultrasonic waves from propagating backward from the piezoelectric transducers. When the ultrasonic probe 12 transmits an ultrasonic wave to an object P, the transmitted ultrasonic wave is sequentially reflected by a discontinuity surface of acoustic impedance of internal body tissue, and is received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by a moving blood flow is subjected to a frequency shift depending on the velocity component of the moving body in the ultrasonic transmission direction due to the Doppler effect.

Assume that the ultrasonic probe 12 according to this embodiment is a one-dimensional array probe (a probe having a plurality of ultrasonic transducers one-dimensionally arrayed along a predetermined direction). However, the ultrasonic probe 12 is not limited to this and may be a two-dimensional array probe (a probe having ultrasonic transducers arranged in the form of a two-dimensional matrix).

The input device 13 is connected to an apparatus main body 11 and includes various types of switches, buttons, a trackball, a mouse, and a keyboard which are used to input, to the apparatus main body 11, various types of instructions, conditions, an instruction to set a region of interest (ROI), various types of image quality condition setting instructions, and the like from the operator. When, for example, the operator operates the end button or freeze button of the input device input device 13, the ultrasonic transmission/reception is terminated, and the ultrasonic diagnostic apparatus is set in a pause state.

The monitor 14 displays morphological information and blood flow information in the living body as images based on video signals from the display processing unit 28.

The ultrasonic transmission unit 21 includes a trigger generation circuit, delay circuit, and pulser circuit (none of which are shown). The trigger generation circuit repeatedly generates trigger pulses for the formation of transmission ultrasonic waves at a predetermined rate frequency fr Hz (period: 1/fr sec). The delay circuit gives each trigger pulse a delay time necessary to focus an ultrasonic wave into a beam and determine transmission directivity for each channel. The pulser circuit applies a driving pulse to the probe 12 at the timing based on this trigger pulse.

The ultrasonic transmission unit 21 has a function of instantly changing a transmission frequency, transmission driving voltage, or the like to execute a predetermined scan sequence in accordance with an instruction from the control processor 28. In particular, the function of changing a transmission driving voltage is implemented by linear amplifier type transmission circuit capable of instantly switching its value or a mechanism of electrically switching a plurality of power supply units.

The ultrasonic reception unit 22 includes an amplifier circuit, A/D converter, and adder (none of which are shown). The amplifier circuit amplifies an echo signal received via the probe 12 for each channel. The A/D converter determines reception directivities of the amplified echo signals and gives them delay times necessary perform reception dynamic focusing. The adder then performs addition processing for the signals. With this addition, a reflection component from a direction corresponding to the reception directivity of the echo signal is enhanced to form a composite beam for ultrasonic transmission/reception in accordance with reception directivity and transmission directivity.

The B-mode processing unit 23 receives an echo signal from the reception unit 22, and performs logarithmic amplification, envelope detection processing, and the like for the signal to generate data whose signal intensity is expressed by a luminance level.

The blood flow detection unit 24 detects a blood flow signal from the echo signal received from the reception unit 22, and generates blood flow data. In general, the blood flow detection unit 24 detects a blood signal by CFM (Color Flow Mapping). In this case, the blood flow detection unit 24 analyzes the blood flow signal to obtain blood flow information such as mean velocities, variances, and powers as blood flow data at multiple points.

The image generation unit 25 generates image data by using the data output from the B-mode processing unit 23 and the blood flow detection unit 24. The image generation unit 25 generates volume data by using the data output from the B-mode processing unit 23 and the blood flow detection unit 24, and performs predetermined image processing such as volume rendering, MPR (Multi Planar Reconstruction), and MIP (Maximum Intensity Projection). Note that for the purpose of reducing noise or smooth concatenation of images, a two-dimensional filter may be inserted after the image generation unit 25 to perform spatial smoothing.

The measurement processing unit 27 executes predetermined measurement processing and the like by using an IMT measurement support function (to be described later).

The display processing unit 28 executes various kinds of processes associated with a dynamic range, luminance (brightness), contrast, y curve correction, RGB conversion, and the like for various kinds of image data generated/processed by the image generation processing unit 25.

The control processor 29 has the function of an information processing apparatus (computer) and controls the operation of the main body of this ultrasonic diagnostic apparatus. The control processor 29 reads out a dedicated program for implementing the IMT measurement support function (to be described later) from the storage unit 31, expands the program in its own memory, and executes computation, control, and the like associated with each type of processing.

The storage unit 30 stores the dedicated program for implementing the IMT measurement support function (to be described later), diagnosis information (patient ID, findings by doctors, and the like), a diagnostic protocol, transmission/reception conditions, a body mark generation program, and other data groups. This storage unit is also used to, for example, store images in the RAW data memory, as needed. It is possible to transfer data in the storage unit 30 to an external peripheral device via the interface unit 31.

The interface unit 31 is an interface associated with the input device 13, a network, and a new external storage device (not shown). The interface unit 31 can transfer, via a network, data such as ultrasonic images, analysis results, and the like obtained by this apparatus to another apparatus.

(IMT Measurement Support Function)

The IMT measurement support function of the ultrasonic diagnostic apparatus 1 will be described next. This function is designed to determine an image in which an ultrasonic scan plane substantially includes the central axis of the target blood vessel when performing IMT measurement, based on the objective quantitative value (feature amount) concerning the target blood vessel.

For the sake of a concrete description, this embodiment will exemplify a case in which the ultrasonic diagnostic apparatus uses the IMT measurement support function. However, the embodiment is not limited to this case, and can implement this IMT measurement support function in, for example, medical image diagnostic apparatuses such as an X-ray computed tomography apparatus, magnetic resonance imaging apparatus, X-ray diagnostic apparatus, and nuclear medicine diagnostic apparatus and a medical workstation (medical image reference apparatus).

For the sake of a concrete description, this embodiment will exemplify a case in which this IMT measurement support processing is executed by using the two-dimensional image data (B-mode data, CFM data, or the like) processed by the image generation processing unit 25. However, it is possible to execute this processing by using each RAW data output from the B-mode processing unit 23 and the blood flow detection unit 24 as data to be processed.

FIG. 2 is a flowchart showing a procedure for processing (IMT measurement support processing) based on this IMT measurement support function. The contents of processing in each step will be described below.

[Input of Patient Information and Like: Step S1]

The operator inputs patient information and selects transmission/reception conditions (a field angle for determining the size of a scan region, a focal position, and a transmission voltage, and the like), an imaging mode (B mode, CFM mode, or the like) for ultrasonically scanning a two-dimensional section including the target blood vessel, a mode (IMT measurement support processing mode) for executing IMT measurement support processing, and the like via the input device 13 (step S1). The storage unit 30 automatically stores the input and selected various kinds of information, conditions, modes, and the like.

[Acquisition/Display of Two-Dimensional Image Data: Step S2]

The operator brings the ultrasonic probe 12 into contact with the body surface of the object at a desired position, and the apparatus ultrasonically scans a two-dimensional section including the target blood vessel as a scan region in the M mode or CFM mode. The echo signal acquired by ultrasonic scanning in the B mode is sent to the B-mode processing unit 23 and the blood flow detection unit 24 via the ultrasonic reception unit 22. The B-mode processing unit 23 generates a plurality of B-mode data by executing logarithmic amplification, envelope detection processing, and the like. The blood flow detection unit 24 generates blood flow data by detecting a blood flow signal from the echo signal received from the ultrasonic reception unit 22. The image generation processing unit 25 generates a B-mode image or blood flow image by using the B-mode data or blood flow data. The display processing unit 28 performs predetermined display processing for each generated image. The monitor 14 displays each image in real time in a predetermined form. The operator adjusts the position of the ultrasonic probe 12 like that shown in FIG. 3, while observing the two-dimensional image displayed in real time, so as to make the ultrasonic scan plane substantially include the central axis of the target blood vessel (step S2).

[Storage of Target Blood Vessel Image: Step S3]

An ultrasonic image (target blood vessel image) corresponding to a plurality of frames concerning the target blood vessel is stored in the cine memory of the image generation processing unit 25 in response to an ECG signal as a trigger. At this time, time information for each image based on an ECG signal is also stored in correspondence with each image (step S3).

[Selection of Images in Same Phase: Step S4]

Figure 6:
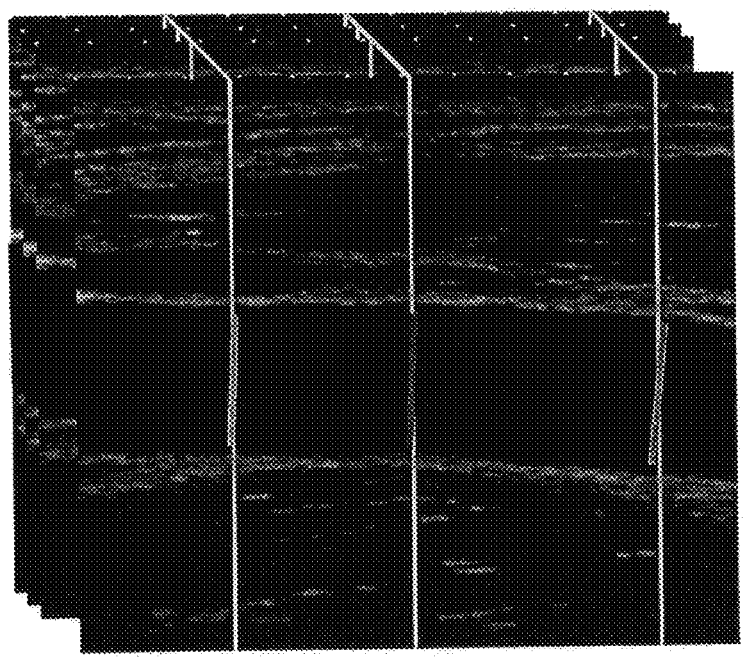
FIG. 6 is a view showing selected target blood vessel images corresponding to the same phase.

The measurement processing unit 27 selects a plurality of target blood vessel images in the same phase (e.g., a phase a predetermined period of time after an R wave) from target blood vessel images corresponding to a plurality of frames stored in the cine memory, based on time information using an ECG signal as a reference signal (see FIG. 6).

[Calculation of Feature Amount: Step S5]

The measurement processing unit 27 extracts a measurement region in each selected target blood vessel image in the same phase. The extraction of this measurement region can be implemented by the following method. Assume that a luminal region is a measurement region. In this case, in a B-mode image, the luminance value (or pixel value) of the measurement region is smaller than that of a neighboring tissue region, and the rate of change in luminance value (the rate of change in pixel value) at the boundary between the measurement region and the remaining region is higher than the rates of change in luminance value at other positions. If, therefore, a target blood vessel image is a B-mode image, it is possible to extract a luminal region by threshold processing with a proper luminance value or a proper rate of change in luminance value. Alternatively, if a target blood vessel image is a CFM image, it is possible to extract a region including a blood flow signal as a measurement region.

Figure 4:
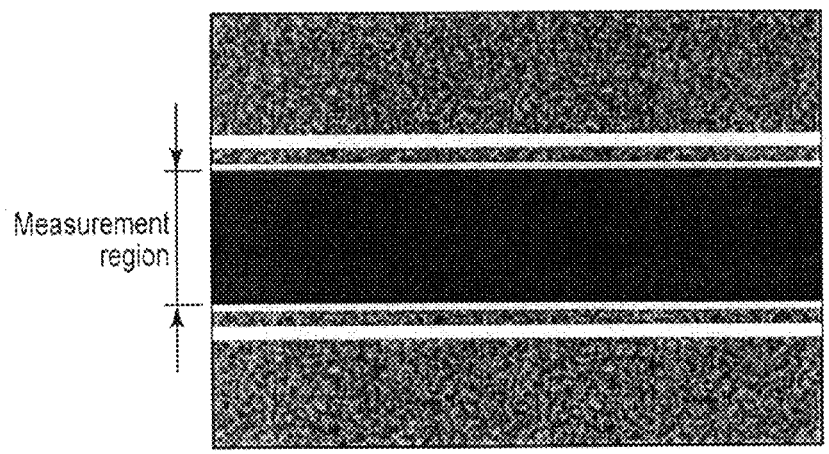
FIG. 4 is a view showing an example of the target blood vessel image without any plaque.
Figure 5:
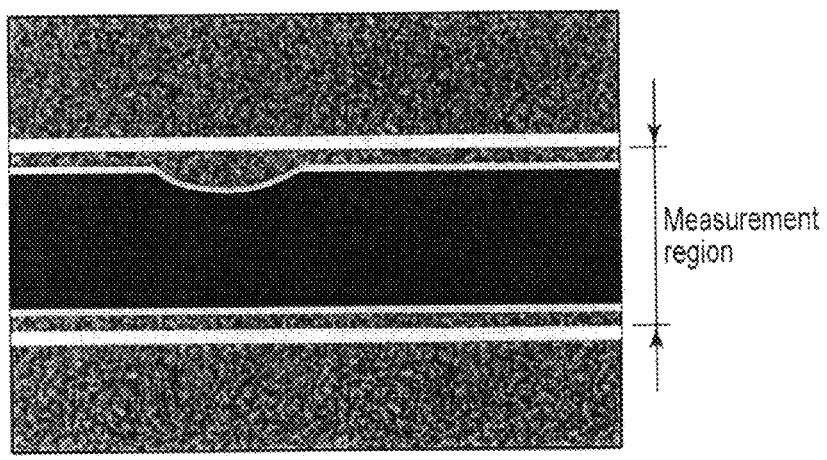
FIG. 5 is a view showing an example of a plurality of target blood vessel images with plaque.

Note that blood vessels as extraction targets in measurement regions include a blood vessel having an almost uniform width as shown in FIG. 4 and a blood vessel with plaque which has a non-uniform width as shown in FIG. 5. In the latter case, the influence of a plaque shape may be reduced by, for example, excluding a plaque region by interpolation processing using information concerning a region adjacent to the plaque or defining a measurement region as a region including not only a luminal region but also the intima of the blood vessel. In addition, this embodiment is not limited to these cases, and it is possible to use an arbitrary measurement region in accordance with an objective quantitative value concerning the target blood vessel.

The measurement processing unit 27 also calculates feature amounts for determining the shift between a two-dimensional section and the central axis of the target blood vessel in the running direction at at least two or more positions in the longitudinal direction of each measurement region for each extracted target blood vessel image (step S5). In this embodiment, as shown in FIG. 6, as the above feature amount, the lateral width of the target blood vessel is used, and feature amounts are calculated at three positions in the longitudinal direction of a measurement region.

[Determination of Optimal Image: Step S6]

Figure 7:
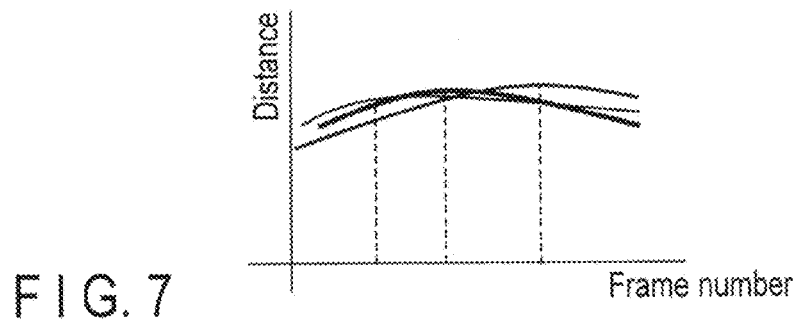
FIG. 7 is a view showing an example of a graph (feature amount curves) representing changes in feature amount of the target blood vessel in the longitudinal direction.

The measurement processing unit 27 generates a graph (feature amount curves) representing changes in feature amount of the target blood vessel in the longitudinal direction by using a plurality of feature amounts obtained by calculation for each selected target blood vessel image in the same phase. FIG. 7 shows an example of a feature amount curve for each target blood vessel image in the same phase.

The measurement processing unit 27 selects a feature amount curve, of a plurality of feature amount curves, which has the maximum feature amount, and determines a target blood vessel image corresponding to the feature amount curve as an image optimal for IMT measurement (an optimal image) (step S6). In this case, the reason why an image corresponding to a feature amount curve having the maximum feature amount is selected as an optimal image is that an image optimal for IMT measurement has the maximum feature amount (the maximum value of the lateral width of the target blood vessel, i.e., the blood vessel diameter) among all the target blood vessel images in the same phase.

Figure 8:
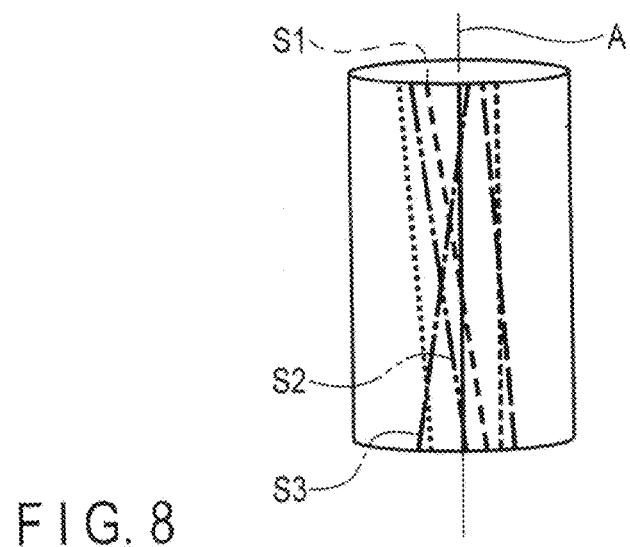
FIG. 8 is a view for explaining the positional relationship between the central axis of the target blood vessel and an ultrasonic scan plane.

Note that if there is a plurality of feature amount curves having the maximum feature amount, an optimal image is determined by the following method. As shown in FIG. 8, the stereoscopic shape of the actual blood vessel can be approximated by a cylindrical shape. If an ultrasonic scan plane completely includes a blood vessel central axis A, a section of the blood vessel (or measurement region) included in the target blood vessel image becomes an almost rectangular shape. For this reason, the respective feature amounts measured at three positions become almost the same value. In contrast to this, if a section crosses the blood vessel central axis A as indicated by S1 to S3 in FIG. 8, the maximum feature amount is measured at only a position where the section crosses the central axis. It is therefore possible to set, as an optimal image, a target blood vessel image corresponding to a feature amount curve, out of a plurality of feature amount curves having the maximum feature amount, which exhibits the minimum rate of change along the longitudinal direction.

[Display of IMT Measurement Result: Step S7]

The measurement processing unit 27 executes IMT measurement by using a determined optimal image. The monitor 14 displays the obtained result in a predetermined form.

This ultrasonic diagnostic apparatus described above calculates feature amounts, used to determine the shift between a two-dimensional section and the central axis of the target blood vessel in the running direction, at at least two or more positions in the longitudinal direction of each measurement region for each target blood vessel image, and determines an image optimal for IMT measurement based on the feature amounts. It is therefore possible to perform IMT measurement by always using an optimal image based on an objective index regardless of the experience of the operator.

Second Embodiment

The second embodiment will be described next. An ultrasonic diagnostic apparatus according to this embodiment determines an optimal image by using, for example, the minor axis length and major axis length of an ellipse obtained by ellipse fitting.

Figure 9:
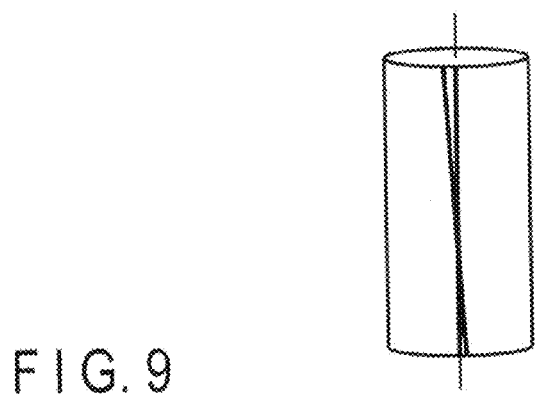
FIG. 9 is a view for explaining the positional relationship between the central axis of the target blood vessel and an ultrasonic scan plane.

As shown in FIG. 9, a section of the cylinder cut by a plane which does not include a central axis A logically has an elliptic shape like that shown in FIG. 10. If a cut surface completely passes over the central axis of the cylinder, it can be thought that the major axis length of an ellipse as a cut surface is infinite. From these points of view, it is possible to evaluate the positional relationship between a blood vessel section cut by a plane and the central axis in accordance with the major axis length obtained by ellipse fitting. That is, the apparatus calculates the longitudinal length and lateral width (i.e., blood vessel diameter) of the measurement region based on all the blood vessel target images in the same phase selected in step S5. Thereafter, as shown in FIG. 10, the apparatus performs ellipse fitting of a blood vessel section of each blood vessel target image, and compares the obtained minor axis length of the ellipse with the blood vessel radius obtained from the blood vessel diameter. If the minor axis length is shorter than the blood vessel radius, the apparatus can determine that the blood vessel section does not pass over the blood vessel central axis. If the minor axis length of the ellipse is almost equal to the blood vessel radius or the major axis length is shorter than a preset threshold, the apparatus can determine that the blood vessel section intersects the central axis at a given angle. If the minor axis length of the ellipse is equal to the blood vessel radius, and the major axis length is longer than the present threshold, the blood vessel section can be considered to substantially include the central axis A.

Even if the minor axis length and major axis length of an ellipse obtained by ellipse fitting of a blood vessel section are set as references (feature amounts), it is possible to determine an optimal image.

Third Embodiment

The third embodiment will be described next. An ultrasonic diagnostic apparatus according to this embodiment determines an optimal image based on the area of a blood flow region, as a feature amount, which is obtained when an ultrasonic image is acquired by CFM (Color Flow Mapping).

Figure 11:
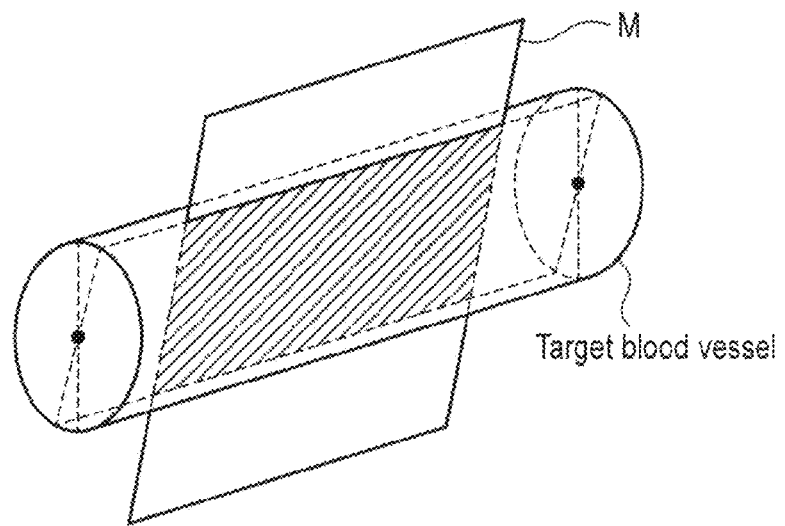
FIG. 11 is a view showing an example of a case in which an ultrasonic scan plane M substantially includes the central axis of the blood vessel.
Figure 12:
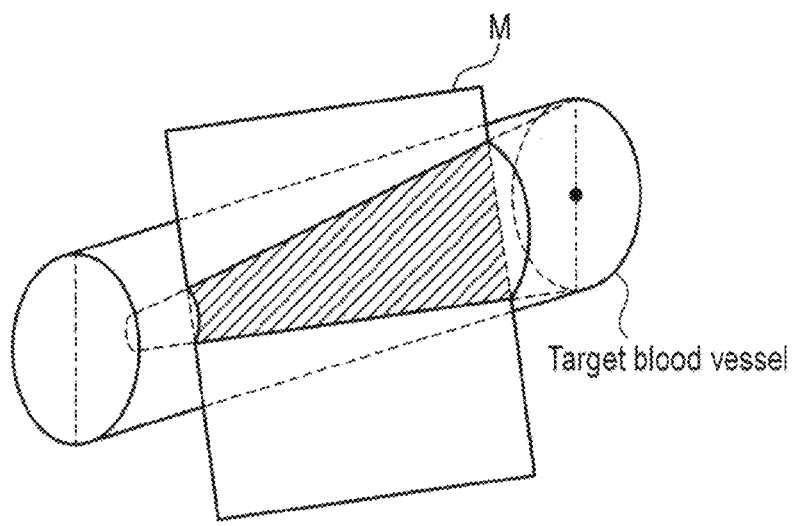
FIG. 12 is a view showing an example of a case in which the ultrasonic scan plane M dose not substantially include the central axis of the blood vessel.

FIG. 11 shows an example of a case in which an ultrasonic scan plane M substantially includes the central axis of the blood vessel. FIG. 12 shows an example of a case in which the ultrasonic scan plane M does not substantially include the central axis of the blood vessel. As is obvious from the comparison between FIGS. 11 and 12, the area of a blood flow region on a CFM image in a case in which the ultrasonic scan plane M substantially includes the blood vessel central axis is always larger than the area of a blood flow region on a CFM image in a case in which the ultrasonic scan plane M does not substantially include the blood vessel central axis.

Figure 13:
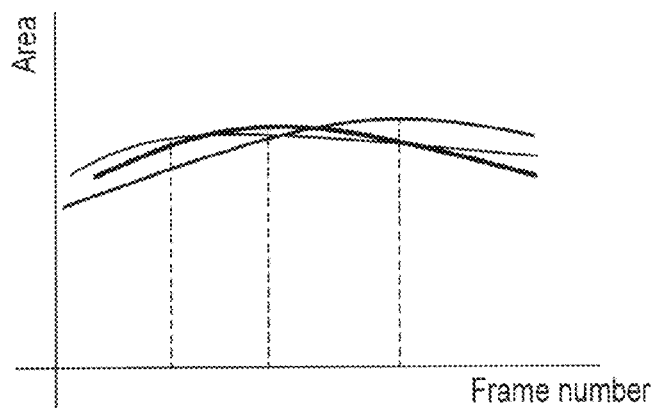
FIG. 13 is a graph showing an example of the feature amount curve obtained by plotting the area of each target blood vessel image in the same phase.

If, therefore, a target blood vessel image is a CFM image, the apparatus extracts a region including a blood flow signal based on at least any one of a flow rate and a power in step S5 described above. In step S6, determining the image in which the extracted region has the largest area can determine an optimal image. FIG. 13 shows an example of the feature amount curve obtained by plotting the area of each target blood vessel image in the same phase.

The method described above allows the operator to perform IMT measurement by always using an optimal image based on an objective index regardless of the influence of the operator.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
   an ultrasonic probe configured to acquire a plurality of ultrasonic data by repeatedly scanning a two dimensional section in a longitudinal direction of a target blood vessel with an ultrasonic wave;
   an image generation processor configured to generate a plurality of ultrasonic images by using the plurality of ultrasonic data; and a measurement processor configured to extract a measurement region based on one of a pixel value and a rate of change in pixel value from each of the ultrasonic images, calculate lateral widths of the measurement region at at least two positions, determine an ultrasonic image having a smallest rate of change in pixel value from the plurality of ultrasonic images based on the lateral widths, and measure an intima media thickness of the target blood vessel by using the ultrasonic image having a smallest rate of change in pixel value.

2. The apparatus of claim 1, wherein the ultrasonic probe acquires the plurality of ultrasonic data in correspondence with a phase of a biological signal which periodically changes by performing the scan in synchronism with the biological signal, the image generation processor generates the plurality of ultrasonic images associated with the phase of the biological signal, and the measurement processor selects a plurality of ultrasonic images corresponding to a predetermined phase from the plurality of ultrasonic images, calculates the lateral widths concerning each selected ultrasonic image, and determines the ultrasonic image having a smallest rate of change in pixel value from the plurality of selected ultrasonic images.

3. The apparatus of claim 2, wherein the biological signal comprises an ECG signal.

4. The apparatus of claim 1, wherein the measurement processor generates a graph indicating a change in the lateral widths of the target blood vessel in a longitudinal direction for each selected ultrasonic image, and determines the ultrasonic image having a smallest rate of change in pixel value based on the plurality of generated graphs.

5. A medical image diagnostic apparatus comprising:

an image generation processor configured to generate a plurality of blood vessel images by using a plurality of blood vessel data obtained by imaging a two dimensional section in a longitudinal direction of a target blood vessel; and a measurement processor configured to extract a measurement region based on one of a pixel value and a rate of change in pixel value of each blood vessel image, calculate lateral widths of the measurement region at at least two positions, a blood vessel image having a smallest rate of change in pixel value from the plurality of blood vessel images based on the lateral widths, and measure an intima media thickness of the target blood vessel by using the blood vessel image having a smallest rate of change in pixel value.

6. The apparatus of claim 5, wherein the plurality of blood vessel data are captured in synchronism with a biological signal which periodically changes and is associated with a phase of the biological signal, the image generation processor generates the plurality of blood vessel images associated with the phase of the biological signal, and the measurement processor selects a plurality of blood vessel images corresponding to a predetermined phase from the plurality of blood vessel images, calculates the lateral widths concerning the each selected blood vessel image, and determines the blood vessel image having a smallest rate of change in pixel value from the plurality of selected blood vessel images.

7. The apparatus of claim 6, wherein the biological signal comprises an ECG signal.

8. The apparatus of claim 5, wherein the measurement processor generates a graph indicating a change in the lateral widths of the target blood vessel in a longitudinal direction for each selected blood vessel image, and determines the blood vessel image having a smallest rate of change in pixel value based on the plurality of generated graphs.

9. An ultrasonic diagnostic apparatus comprising:

an ultrasonic probe configured to acquire a plurality of ultrasonic data by repeatedly scanning a two dimensional section in a longitudinal direction of a target blood vessel with an ultrasonic wave;

an image generation processor configured to generate a plurality of ultrasonic images by using the plurality of ultrasonic data;

a measurement processor configured to calculate a major axis length and minor axis length of an ellipse which are obtained by ellipse fitting of a section of the target blood vessel on each ultrasonic image, determine an ultrasonic image having a minor axis length that substantially equals to a blood vessel radius and a major axis length that is longer than a preset threshold from the plurality of ultrasonic images based on the major axis length and minor axis length, and measure an intima-media thickness of the target blood vessel by using the ultrasonic image having a minor axis length that substantially equals to a blood vessel radius and a major axis length that is longer than a preset threshold.

10. The apparatus of claim 9, wherein the ultrasonic probe acquires the plurality of ultrasonic data in correspondence with a phase of a biological signal which periodically changes by performing the scan in synchronism with the biological signal, the image generation processor generates the plurality of ultrasonic images associated with the phase of the biological signal, and the measurement processor selects a plurality of ultrasonic images corresponding to a predetermined phase from the plurality of ultrasonic images, calculates the major axis length and minor axis length concerning each selected ultrasonic image, and determines the ultrasonic image having a minor axis length that substantially equals to a blood vessel radius and a major axis length that is longer than a preset threshold from the plurality of selected ultrasonic images.

11. The apparatus of claim 10, wherein the biological signal comprises an ECG signal.

12. An ultrasonic diagnostic apparatus comprising:

an ultrasonic probe configured to acquire a plurality of ultrasonic data by repeatedly scanning a two dimensional section in a longitudinal direction of a target blood vessel with an ultrasonic wave;

an image generation processor configured to generate a plurality of color flow mapping images by using the plurality of ultrasonic data; and a measurement processor configured to extract a region including a blood flow signal as a measurement region, calculate an area of the measurement region, determine a color flow mapping image having a largest area from the plurality of color flow mapping images based on the area of the measurement region, and measure an intima-media thickness of the target blood vessel by using the color flow mapping image having a largest area.

13. The apparatus of claim 12, wherein the ultrasonic probe acquires the plurality of ultrasonic data in correspondence with a phase of a biological signal which periodically changes by performing the scan in synchronism with the biological signal, the image generation processor generates the plurality, of color flow mapping images associated with the phase of the biological signal, and the measurement processor selects a plurality of color flow mapping images corresponding to a predetermined phase from the plurality of color flow mapping image, calculates the area of the measurement region concerning each selected color flow mapping image, and determines the color flow mapping image having a largest area from the plurality of selected color flow mapping images.

14. The apparatus of claim 13, wherein the biological signal comprises an ECG signal.

15. A medical image diagnostic apparatus comprising:

an image generation processor configured to generate a plurality of blood vessel images by using a plurality of blood vessel data;

a measurement processor configured to calculate a major axis length and minor axis length of an ellipse which are obtained by ellipse fitting of a section of the target blood vessel on each blood vessel image, determine a blood vessel image having a minor axis length that substantially equals to a blood vessel radius and a major axis length that is longer than a preset threshold from the plurality of blood vessel images based on the major axis length and minor axis length, and measure an intima-media thickness of the target blood vessel by using the blood vessel image having a minor axis length that substantially equals to a blood vessel radius and a major axis length that is longer than a preset threshold.

16. The apparatus of claim 15, wherein the plurality of blood vessel data are captured in synchronism with a biological signal which periodically changes and is associated with a phase of the biological signal, the image generation processor generates the plurality of blood vessel images associated with the phase of the biological signal, and the measurement processor selects a plurality of blood vessel images corresponding to a predetermined phase from the plurality of blood vessel images, calculates the major axis length and minor axis length concerning each selected blood vessel image, and determines the blood vessel image having a minor axis length that substantially equals to a blood vessel radius and a major axis length that is longer than a preset threshold from the plurality of selected blood vessel images.

17. The apparatus of claim 16, wherein the biological signal comprises an ECG signal.

18. A medical image diagnostic apparatus comprising:

an image generation processor configured to generate a plurality of color flow images by using a plurality of ultrasonic data; and a measurement processor configured to extract a region including a blood flow signal as a measurement region, calculate an area of the measurement region, determine a color flow image having a largest area from the plurality of color flow images based on the area of the measurement region, and measure an intima-media thickness of the target blood vessel by using the color flow image having a largest area.

19. The apparatus of claim 18, wherein the plurality of ultrasonic data are captured in synchronism with a biological signal which periodically changes and is associated with a phase of the biological signal, the image generation processor generates the plurality of color flow images associated with the phase of the biological signal, the measurement processor selects a plurality of color flow images corresponding to a predetermined phase from the plurality of color flow image, calculates the area of the measurement region concerning the each selected color flow image, and determines the color flow image having a largest area from the plurality of selected color flow images.

20. The apparatus of claim 19, wherein the biological signal comprises an ECG signal.

* * * * *